(12) United States Patent
Hattori et al.

(10) Patent No.: US 7,618,638 B2
(45) Date of Patent: Nov. 17, 2009

(54) MATRIX METALLOPROTEASE INHIBITOR

(75) Inventors: Koji Hattori, Aichi-ken (JP); Hiroshi Mizutani, Inazawa (JP); Kazuhisa Osumi, Ichinomiya (JP)

(73) Assignee: Nippon Menard Cosmetic Co., Ltd., Nagoya-Shi (JP)

( * ) Notice: Subject to any disclaimer, the term of this patent is extended or adjusted under 35 U.S.C. 154(b) by 185 days.

(21) Appl. No.: 10/490,317

(22) PCT Filed: Sep. 27, 2002

(86) PCT No.: PCT/JP02/10006

§ 371 (c)(1), (2), (4) Date: Oct. 4, 2004

(87) PCT Pub. No.: WO03/028749

PCT Pub. Date: Apr. 10, 2003

(65) Prior Publication Data

US 2005/0037024 A1 Feb. 17, 2005

(30) Foreign Application Priority Data

Sep. 27, 2001 (JP) ............................ 2001-297672

(51) Int. Cl.
*A01N 65/00* (2006.01)
(52) U.S. Cl. ................................ 424/195.15
(58) Field of Classification Search ........................ None
See application file for complete search history.

(56) References Cited

FOREIGN PATENT DOCUMENTS

| CN | 1157151 A | * | 8/1997 |
|----|-----------|---|--------|
| CN | 1291511 A |   | 4/2001 |
| JP | 62-239953 |   | 10/1987 |
| JP | 6-345636  |   | 12/1994 |
| JP | 8-73369   |   | 3/1996 |
| JP | 9-40552   |   | 2/1997 |
| JP | 9-235293  |   | 9/1997 |
| JP | 11-139947 |   | 5/1999 |
| JP | 11-139947 |   | 7/1999 |
| JP | 11180889 A2 |  | 7/1999 |

OTHER PUBLICATIONS

Furusawa et al Phytotherapy Res, 1992, 6:300-304.*
Yongfa et al., "The Preparation of a Solid Extract of Tai Mountain Ganoderma Lucidum," Weifang Medical School Journal 2001 vol. 23 No. 1.
Zhang et al., The Formulation Design and Development Pathway of Dark Colored Foods, Chinese Food and Nutrition Mar. 1999.
Chinese Office Action dated Jul. 22, 2005 from corresponding Japanese Application (English Translation included).
Russian Office Action dated Mar. 18, 2005 from corresponding Russian Application (English Translation included).
Lovy et al., "Activity of Edible Mushrooms Against the Growth of Human $T_4$ Leukemic Cancer Cells, HeLa Cervical Cancer Cells, and Plasmodium falciparum", 1999, Journal of Herbs, Spices & Medicinal Plants, vol. 6(4).
Yip et al., "Matrix metalloproteinase inhibitors: applications in oncology", 1999, Investigational New Drugs.
Canadian Office Action dated Oct. 19, 2006, from corresponding Canadian Application No. 2,460,834.
Tanaka et al., "Effects of Magojakushi and Reishi on the production of collagen and glysosaminoglycans in cultured human dermal fibroblasts", 1992, Journal of Medical and Pharmaceutical Society for Wakan-Yaku, vol. 9, No. 3, pp. 209-213.
Morigiwa et al., "Angiotensin Converting Enzyme-Inhibitory Triterpenes from *Ganoderma lucidum*", 1986, Chem. Pharm. Bull., vol. 34, No. 7, pp. 3025-3028.
Choj et al., "Fibrinolytic and antithrombotic protease from *Ganoderma lucidum*", 2000, Mycologia, vol. 92, No. 3, pp. 545-552.
Okamoto et al., Black Reishi (*Ganoderma lucidum*, Black), 1997, Food Reviews International, vol. 13, No. 3, pp. 370-373.
Schoenermark, et al., "Retinoid-Mediated Suppression of Tumor Invasion and Matrix Metalloproteinase Synthesis", 2001, Annals New York Academy of Sciences, pp. 465-485.
"Brewing Society of Japan", vol. 85, No. 6, pp. 385-392, issued in 1990 (partial translation).
"Anti-invasive activity of torilin, a sesquiterpene compound isolated from *Torilis japonica*", Kim MS, Baek JH, Park MT, Sohn TK, Kim SE, Lee JJ, Kim KW, Oncol Rep, Mar.-Apr. 2001; 8(2):359-64, Abstract.

* cited by examiner

*Primary Examiner*—Christopher R. Tate
*Assistant Examiner*—Deborah A. Davis
(74) *Attorney, Agent, or Firm*—Weaver Austin Villeneuve & Sampson LLP

(57) ABSTRACT

The object of the present invention is to provide a preventive and relieving medicine for activated matrix metalloproteinase-causing disorders and diseases, which contains a solvent extract of *Ganoderma* mushroom.

The preventive and relieving medicine for activated matrix metalloproteinase (MMP)-causing disorders and diseases according to the present invention contains the solvent extract of *Ganoderma* mushroom. The solvent extract of *Ganoderma* mushroom has MMP inhibiting behaviors and is effective for prevention, suppression, and symptomatic relief of various activated MMP-causing disorders and diseases, such as metastasis of cancers, ulceration, rheumatoid arthritis, osteoporosis, periodontitis, and aging of skin.

15 Claims, No Drawings

MATRIX METALLOPROTEASE INHIBITOR

TECHNICAL FIELD

The present invention relates to a matrix metalloproteinase (MMP) inhibitor. More specifically the invention pertains to an MMP inhibitor that has high safety and is expected to have effects on prevention, suppression, and symptomatic relief of various activated MMP-causing disorders and diseases, such as metastasis of cancers, ulceration, rheumatoid arthritis, osteoporosis, periodontitis, and aging of skin.

BACKGROUND ART

Cancer is one of the primary causes of death in most advanced countries. In Japan, the cancer occupies almost 30% of the cause of death. Advancement of surgical treatment and radio therapeutics often allows for removal of the primary focus of a cancer. The still high morbidity is ascribed to the metastatic properties of cancers. In the current state, it is extremely difficult to cure the cancer with multiple metastases. One of the important targets of cancer treatment is thus to establish a method of suppressing metastasis of cancer, in addition to the conventional treatment of the primary focus. In this state, the mechanism of cancer metastasis is gradually being elucidated on the molecular level. The decomposition system of the extracellular matrixes has been noted as one of the metastatic processes.

Metastasis of a cancer represents the state that cancer cells released from a primary site are distributed to the whole body through the blood stream, are delivered live to another organ, and start multiplication in the tissue of the organ. In general, the tumor tissue is surrounded by a dense extracellular matrix. Enzymolysis of the extracellular matrix is necessary for distribution of cancer cells from the primary site. The extracellular matrix is composed of various macromolecules including collagen, elastin, fibronectin, laminin, and proteoglycan. MMP is a group of primary enzymes involved in enzymolysis of the extracellular matrixes. The MMP is activated and has enhanced enzyme expression in the process of vascularization in the cancer tissue or in the process of metastasis of the cancer, as described in Reference 1 cited below. A decrease in enzyme expression and inhibition of the enzymatic activity are thus expected to suppress invasion of cancer cells and thereby metastasis of cancers.

Reference 1
'Retinoid-Mediated Suppression of Tumor Invasion and Matrix Metalloproteinase Synthesis', Shoenermark M. P. et al, Annals New York Academy of Sciences, Vol. 878, pp 466-486, 1999

In the process of invasion of cancer cells into the macromolecules, collagenolysis is especially a critical step. Decomposition of the type IV collagen present on the basilar membrane of a blood vessel is necessary to allow cancer cells to invade into the blood vessel or to be released from the blood vessel. Liotta et al has found that the action of the type IV collagenolytic enzyme secreted by the cancer cells is an important factor to determine the cancer metastasis power. Gelatinase included in the MMP is an enzyme produced by fibroblasts, endothelial cells, and cancer cells and decomposes the matrixes of the type IV collagen, gelatin, and elastin. A substance having the inhibiting activity, for example, against gelatinase is expected to have the effects of suppressing vascularization in the cancer tissues and metastasis of cancers and to be effective for prevention and treatment of cancers and carcinomas.

Reference 2
'Metastatic potential correlates with enzymatic degradation of basement membrane collagen', Liotta L. A. et al, Nature, Vol. 284, pp 67-68, 1980

The reference 3 cited below has reported that the MMP plays an important role in decomposition of extracellular matrixes in various pathology including cancers, ulceration, rheumatoid arthritis, osteoporosis, and periodontitis. The activated MMP due to external stimuli like ultraviolet radiation decomposes essential components for maintaining the skin structure. The MMP has thus been specifically noted recently as an aging acceleration factor activated by ultraviolet radiation.

Reference 3
'Matrix metalloproteinases as tissue destructive proteinases', Mitsutoshi Nakata, Yasunori Okada, KOKYU (Respiratory), Vol. 18, No. 4, pp 365-371, 1999

The MMP inhibitors have thus been expected to have effects on treatment and symptomatic relief of the activated MMP-causing disorders and diseases and have been intensively studied for screening. Such inhibitors are disclosed in the following references:

JAPANESE PATENT LAID-OPEN GAZETTE No. 9-40552
JAPANESE PATENT LAID-OPEN GAZETTE No. 11-147833
PATENT LAID-OPEN GAZETTE No. 2000-226311

The object of the present invention is thus to provide an MMP inhibitor that has inhibiting activity against activation of MMP produced by high metastatic carcinoma cell strains and is effective for prevention and symptomatic relief of various activated MMP-causing disorders and diseases, such as metastasis of cancers.

DISCLOSURE OF THE IVNENTION

The inventors of the present invention targeted plant extracts having high safety and carried out screening of the plant extracts for the MMP inhibiting activity. As a fruit of the extensive studies, the inventors have found that solvent extracts of *Ganoderma* mushrooms have excellent MMP inhibition effects and high cancer metastasis suppression effects in experiments on lung-metastasized animal models, and have completed the present invention. At least part of the above and the other related objects is thus attained by an MMP inhibitor, which includes a solvent extract of *Ganoderma* mushroom as an active ingredient.

The present invention is also directed to any of medicines, drugs, pharmaceutical products, quasi drugs, cosmetics, toilet articles, and food products, which includes a solvent extract of *Ganoderma* mushroom and is applied for prevention, suppression, or symptomatic relief of activated MMP-causing disorders and diseases.

BEST MODES OF CARRYING OUT THE INVENTION

Embodiments of the present invention are discussed below. *Ganoderma* mushrooms used in the present invention are basidiomycetes applied for galenicals 'Reishi' and belong to *Ganoderma*, Ganodermataceae. The *Ganoderma* mushrooms include *Ganoderma lucidum* (Reishi), *Ganoderma atrum*, and *Ganoderma sinense* (according to the nomenclature in the cited reference Acta Microbiologica *Sinica,* 19(3), 265-279, 1979), although this classification is not restrictive. The *Ganoderma* mushrooms used in the present invention may be any of commercially available ones in Chinese and Japanese markets. Among the *Ganoderma* mushrooms, *Ganoderma lucidum* (Reishi) and *Ganoderma atrum* are preferable, and *Ganoderma atrum* is most preferable.

Available examples of an extractant include water, lower monohydric alcohols (for example, methanol, ethanol, 1-propanol, 2-propanol, 1-butanol, and 2-propanol), liquid polyhydric alcohols (for example, 1,3-butylene glycol, propylene glycol, and glycerol), ketones (for example, acetone and methyl ethyl ketone), acetonitrile, esters (for example, ethyl acetate andbutyl acetate), hydrocarbons (for example, hexane, heptane, and liquid paraffin), and ethers (for example, ethyl ether, tetrahydrofuran, and propyl ether). Preferable are polar solvents like water, lower alcohols, and ketones. The extractant may be one solvent or a mixture of two or more solvents. In the case of medicines for internal application, any solvent suitable for internal application may be selected.

The content of the solvent extract of *Ganoderma* mushroom is not specifically restricted, but is in a range of 0.0005 to 10.0% by weight or preferably in a range of 0.005 to 5.0% by weight as a dried weight to the whole weight of any of medicines, drugs, pharmaceutical products, quasi drugs, cosmetics, toilet articles, and food products for prevention, suppression, or symptomatic relief of activated MMP-causing disorders and diseases. The content of less than 0.0005% by weight does not ensure sufficient effects of the present invention. The content of greater than 10.0% by weight, on the other hand, does not further enhance the effects and is thus uneconomical.

The solvent extract of *Ganoderma* mushroom may be used in the form of an extracted solution without any further treatment or with any required treatment, such as concentration, dilution, filtration, or decoloration and deodorization with active carbon or the like. The extracted solution may be evaporated to dryness, spray dried, or freeze dried according to the requirements.

The MMP inhibitor of the present invention may be any of medicines, drugs, pharmaceutical products, quasi drugs, cosmetics, toilet articles, and food products, which contain the solvent extract discussed above and a reapplied for prevention, suppression, or symptomatic relief of activated MMP-causing disorders and diseases. The MMP inhibitor may include diverse additives, which are components generally added to medicines, drugs, pharmaceutical products, quasi drugs, cosmetics, toilet articles, and food products, in a specific range that does not damage the effects of the solvent extract. The additives include fillers, stabilizers, preservatives, binding agents, disintegrants, hydrocarbons, fatty acids, alcohols, esters, surface active agents, metal soaps, pH regulators, antiseptics, flavoring ingredients, moisture retention agents, powder agents, UV absorbents, thickening agents, coloring matters, antioxidants, whitening agents, chelating agents, oils, fats, and waxes.

Available examples of the dosage form in the present invention include powders, pills, tablets, injectable solutions, suppositories, emulsions, capsules, granules, liquids (including tinctures, fluid extracts, alcoholic liquids, suspensions, and limonades), toilet lotions, creams, milkylotions, gels, aerosols, oils, conditioning agents, cleansing agents, bath agents, foundation agents, powders, lipsticks, ointments, poultices, cataplasms, pastes, plasters, extracts, tablet foods, and drinks.

Some examples of the present invention are discussed below. These examples are not at all restrictive but only illustrative. In the compositions of the respective examples, the term 'parts' represents 'parts by weight' unless otherwise specified.

Preparation 1: Hot Water Extract of *Ganoderma atrum*

The process added 400 ml of purified water to 20 g of dried *Ganoderma atrum*, carried out extraction at 95 to 100° C. for 2 hours, and filtered the extracted solution. The filtrate was concentrated and freeze dried to yield 1.4 g of hot water extract of *Ganoderma atrum*.

Preparation 2: 50% Ethanol Extract of *Ganoderma atrum*

The process added 900 ml of a 50% ethanol solution to 100 g of dried *Ganoderma atrum*, carried out extraction at room temperature for 7 days, and filtered the extracted solution. The filtrate was evaporated to dryness to yield 1.9 g of 50% ethanol extract of *Ganoderma atrum*.

Preparation 3: Ethanol Extract of *Ganoderma atrum*

The process added 900 ml of ethanol to 100 g of dried *Ganoderma atrum*, carried out extraction at room temperature for 7 days, and filtered the extracted solution. The filtrate was evaporated to dryness to yield 1.5 g of ethanol extract of *Ganoderma atrum*.

Preparation 4: Hot Water Extract of *Ganoderma lucidum* (Reishi)

The process added 400 ml of purified water to 20 g of dried *Ganoderma lucidum* (Reishi), carried out extraction at 95 to 100° C. for 2 hours, and filtered the extracted solution. The filtrate was concentrated and freeze dried to yield 2.0 g of hot water extract of *Ganoderma lucidum* (Reishi).

Preparation 5: 50% Ethanol Extract of *Ganoderma lucidum* (Reishi)

The process added 900 ml of a 50% ethanol solution to 100 g of dried *Ganoderma lucidum* (Reishi), carried out extraction at room temperature for 7 days, and filtered the extracted solution. The filtrate was evaporated to dryness to yield 3.1 g of 50% ethanol extract of *Ganoderma lucidum* (Reishi).

Preparation 6: Ethanol Extract of *Ganoderma lucidum* (Reishi)

The process added 900 ml of ethanol to 100 g of dried *Ganoderma lucidum* (Reishi), carried out extraction at room temperature for 7 days, and filtered the extracted solution. The filtrate was evaporated to dryness to yield 2.5 g of ethanol extract of *Ganoderma lucidum* (Reishi).

EXAMPLE 1

Powder 1

| Prescription | Contents |
| --- | --- |
| 1. Hot water extract of *Ganoderma atrum* (Preparation 1) | 2.0 parts |
| 2. Dried corn starch | 38.0 |
| 3. Microcrystalline cellulose | 60.0 |

The process mixes the components 1 to 3 together to yield a powder 1.

EXAMPLE 2

Powder 2

A powder 2 is prepared by replacing the hot water extract of *Ganoderma atrum* in Example 1 with the 50% ethanol extract of *Ganoderma atrum* (Preparation 2).

EXAMPLE 3

Powder 3

A powder 3 is prepared by replacing the hot water extract of *Ganoderma atrum* in Example 1 with the hot water extract of *Ganoderma lucidum* (Reishi) (Preparation 4).

EXAMPLE 4

Powder 4

A powder 4 is prepared by replacing the hot water extract of *Ganoderma atrum* in Example 1 with an equal amount mixture of the hot water extract of *Ganoderma atrum* (Preparation 1) and the hot water extract of *Ganoderma lucidum* (Reishi) (preparation 4).

COMPARATIVE EXAMPLE 1

Powder A (Powder without the Solvent Extract of *Ganoderma* Mushroom)

A powder A is prepared by replacing the hot water extract of *Ganoderma atrum* in Example 1 with dried corn starch.

EXAMPLE 5

Tablets

| Prescription | Contents |
| --- | --- |
| 1. Ethanol extract of *Ganoderma atrum* (Preparation 3) | 5.0 parts |
| 2. Dried corn starch | 25.0 |
| 3. Carboxymethylcellulose calcium | 20.0 |
| 4. Microcrystalline cellulose | 40.0 |
| 5. Polyvinyl pyrrolidone | 7.0 |
| 6. Talc | 3.0 |

[Manufacturing Process]

The process mixes the components 1 to 4 together, and adds an aqueous solution of the component 5 as a binding agent to the mixture to form granules. The process subsequently adds the component 6 to the granules and forms tablets. The weight of each tablet is 0.52 g.

EXAMPLE 6

Tablet Food

| Prescription | Contents |
| --- | --- |
| 1. 50% Ethanol extract of *Ganoderma lucidum* (Preparation 5) | 2.0 parts |
| 2. Dried corn starch | 50.0 |
| 3. Erythritol | 40.0 |
| 4. Citric acid | 5.0 |
| 5. Sucrose fatty acid ester | 3.0 |
| 6. Flavoring ingredient | Adequate quantity |
| 7. Water | Adequate quantity |

[Manufacturing Process]

The process mixes the components 1 to 4 and 7 and forms granules. The process subsequently adds the components 5 and 6 to the granules and forms tablets. The weight of each table is 1.0 g.

EXAMPLE 7

Drink

| Prescription | Contents |
| --- | --- |
| 1. Ethanol extract of *Ganoderma lucidum* | 1.0 parts |
| 2. Stevia | 0.05 |
| 3. Malic acid | 5.0 |
| 4. Flavoring ingredient | 0.1 |
| 5. Water to make the whole quantity equal to | 100 parts |

[Manufacturing Process]

The process dissolves the components 2 and 3 in a small quantity of water and mixes the components 1, 4, and 5 with the solution.

The following describes experimental examples for the detailed discussion of the effects of the present invention.

EXPERIMENTAL 1

MMP Inhibition Test

The solvent extracts of *Ganoderma* mushrooms were subjected to an inhibition test against gelatinase activity by gelatin zymography. The procedure prepared a 10% SDS-PAGE gel (1 mm thick) containing 0.6 mg/ml gelatin, and made 0.014 ml of a culture supernatant of B16 mouse melanoma cells subjected to gel electrophoresis under non-reducing conditions. The procedure subsequently washed the gel twice with a 2.5% Triton X-100 (Sigma Chemical Co.) solution at room temperature for 30 minutes for removal of SDS, and incubated the washed gel in a 30 mM tris-HCl buffer solution (pH 7.6) containing 200 ml sodium chloride, 5 mM calcium chloride, and 0.01% brij-35 (Sigma Chemical Co.) at 37° C. for 24 hours. Each of the hot water extract of *Ganoderma atrum* (Preparation 1), the hot water extract of *Ganoderma lucidum* (Reishi) (Preparation 4), and the equal amount mixture of the hot water extract of *Ganoderma atrum* and the hot water extract of *Ganoderma lucidum* (Reishi) was added to the buffer solution, in which the gel was soaked. On completion of the reaction, the gel was stained with a 0.2% Coomassie Brilliant Blue R solution and was decolorized with a 5% methanol-7.5% acetic acid solution. The procedure determined the gelatinase activity detected as a non-stained band on the blue stained gel with a densitometer (Atto Densitograph AE-6905, Atto Co.) and calculated the rate of inhibition. The rate of inhibition (%) was calculated according to Equation (1) given below from the observed values of the densitometer. The results are shown in Table 1. The solvent extracts of *Ganoderma* mushrooms inhibited gelatinase produced by the B16 mouse melanoma cells in a concentration dependent manner.

$$\text{Rate of Inhibition} = \{1-(A/B)\} \times 100 \qquad (1)$$

A: Observed value of the densitometer in the case of addition of the solvent extract of *Ganoderma* mushroom B. Observed value of the densitometer in the case of no addition of the solvent extract of *Ganoderma* mushroom

TABLE 1

| Samples | Final Concentration in Reaction Solution [%] | Rate of Inhibition [%] |
|---|---|---|
| S1 | 0.25 | 38 |
|  | 0.50 | 64 |
|  | 1.0 | 99 |
| S2 | 0.25 | 9 |
|  | 0.50 | 49 |
|  | 1.0 | 96 |
| S3 | 0.25 | 26 |
|  | 0.50 | 58 |
|  | 1.0 | 98 |

S1: Hot water extract of *Ganoderma atrum* (Preparation 1)
S2: Hot water extract of *Ganoderma lucidum* (Reishi) (Preparation 4)
S3: Equal amount mixture of hot water extract of *Ganoderma atrum* and hot water extract of *Ganoderma lucidum* (Reishi)

EXPERIMENTAL 2

MMP Inhibition Test

The 50% ethanol extract of *Ganoderma lucidum* (Reishi) (Preparation 5), the ethanol extract of *Ganoderma lucidum* (Reishi) (Preparation 6), the 50% ethanol extract of *Ganoderma atrum* (Preparation 2), and the ethanol extract of *Ganoderma atrum* (Preparation 3) were also subjected to the above inhibition test. The results are shown in Table 2. The final concentrations of these four extracts in the respective reaction solutions were all extremelylowas 0.03%. The ethanol extracts of *Ganoderma* mushrooms at this lower concentration, however, more effectively inhibited gelatinase produced by the B16 mouse melanoma cells, compared with their hot water extracts.

TABLE 2

| Samples | Final Concentration in Reaction Solution[%] | Rate of Inhibition [%] |
|---|---|---|
| T1 | 0.03 | 67 |
| T2 | 0.03 | 78 |
| T3 | 0.03 | 85 |
| T4 | 0.03 | 96 |

T1: 50% Ethanol extract of *Ganoderma lucidum* (Reishi) (Preparation 5)
T2: Ethanol extract of *Ganoderma lucidum* (Reishi) (Preparation 6)
T3: 50% Ethanol extract of *Ganoderma atrum* (Preparation 2)
T4: Ethanol extract of *Ganoderma atrum* (Preparation 3)

EXPERIMENTAL 2

Cancer Metastasis Suppression Test

Each of the hot water extract of *Ganoderma atrum* (Preparation 1), the hot water extract of *Ganoderma lucidum* (Reishi) (Preparation 4), and the equal amount mixture of the hot water extract of *Ganoderma atrum* and the hot water extract of *Ganoderma lucidum* (Reishi) was repeatedly administered at a concentration of 100 mg/kg to one group of C57BL/6 mice through the abdominal cavity once a day for 1 week. Physiological saline was administered to a control group of mice through the abdominal cavity. Each group included 8 mice in this example. B16 mouse melanoma cells were then injected into each mouse through the tail vein to a density of $1 \times 10^5$ cells per mouse. After the injection, the repeated administration of each sample was continued. The lung was extracted from each mouse 3 weeks after the inoculation of the cancer cells and was fixed in a 10% formalin solution. The procedure divided the formalin-fixed lung into 5 lobes and counted the number of metastasized cell nests on the surface of the lobes. The results are shown in Table 3. Administration of the solvent extracts of *Ganoderma* mushrooms significantly suppressed formation of the metastasized cell nests, compared with the control group. Namely the solvent extracts of *Ganoderma* mushrooms had sufficient metastasis resistance.

TABLE 3

| Samples | Average Number of Metastasized Cell Nests |
|---|---|
| U1 | 49 |
| U2 | 8 |
| U3 | 25 |
| U4 | 14 |

U1: Physiological saline
U2: Hot water extract of *Ganoderma atrum* (Preparation 1)
U3: Hot water extract of *Ganoderma lucidum* (Reishi) (Preparation 4)
U4: Equal amount mixture of hot water extract of *Ganoderma atrum* and hot water extract of Ganoderma lucidum (Reishi)

According to the above results, the hot water extract of *Ganoderma atrum* (Preparation 1), the hot water extract of *Ganoderma lucidum* (Reishi) (Preparation 4), and the equal amount mixture of the hot water extract of *Ganoderma atrum* and the hot water extract of *Ganoderma lucidum* (Reishi) had the excellent effects of MMP inhibition and cancer metastasis suppression. The 50% ethanol extracts and the ethanol extracts of *Ganoderma atrum* and *Ganoderma lucidum* (Reishi) (Preparations 2, 3, 5, and 6) were also subjected to the above suppression test. The results showed that the 50% ethanol extracts and the ethanol extracts of these *Ganoderma* mushrooms also had the excellent effects of MMP inhibition and cancer metastasis suppression.

EXPERIMENTAL 3

Cancer Metastasis Suppression Test

Experimental feeding stuffs were prepared by adding each of the powders 1 through 4 (Example 1 through 4) of the present invention, which respectively contained the hot water extract of *Ganoderma atrum* (Preparation 1), the 50% ethanol extract of *Ganoderma atrum* (Preparation 2), the hot water extract of *Ganoderma lucidum* (Reishi) (Preparation 4), and the equal amount mixture of the hot water extract of *Ganoderma atrum* and the hot water extract of *Ganoderma lucidum* (Reishi), at a concentration of 5.0% to a commercially available feeding stuff (MF for breeding mice and rats: Oriental Yeast Co., Ltd.). Groups of mice freely ate the respective feeding stuffs. Another group of mice freely ate an experimental feeding stuff having 5.0% of the powder A (Comparative Example 1) without any solvent extract of *Ganoderma* mushroom (control group). In this example, each group included 8 mice. Like the procedure of Experimental 2, the cancer cells were inoculated 2 weeks after the start of breeding the mice with the powder-added feeding stuffs. The number of metastasized cell nests was counted. The results are shown in Table4. Addition of each powder containing the solvent extract of *Ganoderma* mushroom to the feeding stuff significantly suppressed formation of the metastasized cell nests, compared with the control group (Comparative Example). Namely the solvent extracts of the *Ganoderma* mushrooms were effective for suppression of the cancer metastasis.

TABLE 4

| Samples | Average Number of Metastasized Cell Nests |
|---|---|
| V1 | 62 |
| V2 | 35 |
| V3 | 33 |
| V4 | 47 |
| V5 | 41 |

V1: Comparative Example
V2: Powder 1 (Example 1)
V3: Powder 2 (Example 2)
V4: Powder 3 (Example 3)
V5: Powder 4 (Example 4)

Each of the tablets of Example 5 and the tablet food of Example 6 was crushed into powder in a mortar. The powdered samples were subjected to the above suppression test for the powders. With regard to the drink of Example 7, 0.3 ml of the sample was orally administered to each mouse once a day with a stomach Sonde scope, and the effects of the sample on the cancer metastasis were examined. The samples of Examples 5 through 7 were also effective for suppression of the cancer metastasis.

INDUSTRIAL APPLICABILITY

As described above, the solvent extracts of *Ganoderma* mushrooms have the effects of inhibiting activation of MMP produced by cancer cells as well as the effects of suppressing the cancer metastasis relating to the activated MMP. The MMP inhibitor of the present invention is preferably applied for prevention, suppression, and symptomatic relief of various activated MMP-causing disorders and diseases, such as metastasis of cancers, ulceration, rheumatoid arthritis, osteoporosis, periodontitis, and aging of skin.

The invention claimed is:

1. A pharmaceutical or cosmetic composition having matrix metalloproteinase inhibiting activity comprising an effective amount of a solvent extract of *Ganoderma atrum*, whereby the solvent used to obtain the extract is selected from the group consisting of water, a lower alcohol, a liquid polyhydric alcohol, or mixtures thereof, and wherein the pharmaceutical or cosmetic composition is provided in a form selected from the group consisting of a powder, a tablet, a pill, a suppository, an emulsion, a capsule, a granule, a lotion, a cream, a gel, an aerosol, a lipstick, an ointment, a poultice, a paste, and an adhesive bandage.

2. The pharmaceutical composition of claim 1, wherein the extractant solvent is selected from the group consisting of water, ethanol and mixtures thereof.

3. The pharmaceutical composition of claim 1, wherein the pharmaceutical composition comprises 0.0005%-10% of *Ganoderma Atrum* extract by weight.

4. The pharmaceutical composition of claim 1, wherein the pharmaceutical composition is effective in reducing metastasis in a subject.

5. The cosmetic composition according to claim 1, wherein the cosmetic composition further comprises an additive selected from the group consisting of a filler, a stabilizer, a surface active agent, a colorant, an antioxidant, a UV absorbent, a whitening agent, and a chelating agent.

6. A method for reducing cancer metastasis in a subject in need thereof, the method comprising administering an effective amount of the pharmaceutical composition according to claim 1 to said subject.

7. The pharmaceutical composition of claim 1, wherein the pharmaceutical composition is provided in a form of a tablet or a pill.

8. The pharmaceutical composition of claim 1, wherein the pharmaceutical composition is provided in a form of a suppository.

9. The pharmaceutical composition of claim 1, wherein the pharmaceutical composition is provided in a form of a lipstick.

10. The pharmaceutical composition of claim 1, wherein the pharmaceutical composition is provided in a form of a capsule.

11. The pharmaceutical composition of claim 1, wherein the pharmaceutical composition is provided in a form of a emulsion.

12. The cosmetic composition of claim 1, wherein the cosmetic composition is provided in the form of a lipstick.

13. The cosmetic composition of claim 1, wherein the cosmetic composition further comprises a fatty acid.

14. The cosmetic composition of claim 1, wherein the cosmetic composition further comprises a chelating agent.

15. The pharmaceutical composition of claim 1, wherein the composition further comprises an additive selected from the group consisting of starch, cellulose and talc.

* * * * *